United States Patent [19]

Knapp, Jr. et al.

[11] Patent Number: 4,950,228
[45] Date of Patent: Aug. 21, 1990

[54] URETERAL STENT

[76] Inventors: Peter M. Knapp, Jr., 1801 N. Senate Blvd., Suite 655; Daniel M. Newman, 1801 N. Senate Blvd., both of Indianapolis, Ind. 46202

[21] Appl. No.: 463,297
[22] Filed: Jan. 10, 1990
[51] Int. Cl.$^5$ ............................................. A61M 25/00
[52] U.S. Cl. ........................................ 604/8; 604/281; 604/54
[58] Field of Search ....................................... 604/8–10, 604/54, 55, 93, 280–284

[56] References Cited

U.S. PATENT DOCUMENTS

| | | | |
|---|---|---|---|
| 4,531,933 | 7/1985 | Norton et al. | 604/281 X |
| 4,568,338 | 2/1986 | Todd | 604/281 |
| 4,643,716 | 2/1987 | Drach | 604/281 X |
| 4,694,838 | 9/1987 | Wijayarthna et al. | 604/658 |
| 4,738,667 | 4/1988 | Galloway | 604/281 |
| 4,747,840 | 5/1988 | Ladika et al. | 604/281 |
| 4,790,810 | 12/1988 | Pugh, Jr. et al. | 604/8 |
| 4,887,996 | 12/1989 | Bengmark | 604/54 |

Primary Examiner—Robert A. Hafer
Assistant Examiner—Lynda M. Cofsky
Attorney, Agent, or Firm—Woodard, Emhardt, Naughton Moriarty & McNett

[57] ABSTRACT

A ureteral stent includes a tubular member of substantially uniform outside diameter, the tubular member having proximal and distal ends connected by a body portion, the proximal end including a retention curve to retain the proximal end in the bladder, and the distal end having three portions, the first portion extending from the stent body and being substantially straight, the second portion extending from the first portion and being in the shape of a 360° helical curve having an outside radius, and the third portion extending from the second portion and terminating in a distal tip, the third portion being substantially straight and parallel to the first portion and having a length between 1.2 and 2.0 times the outside radius of the helical curl.

8 Claims, 2 Drawing Sheets

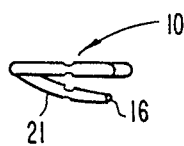
Fig.3
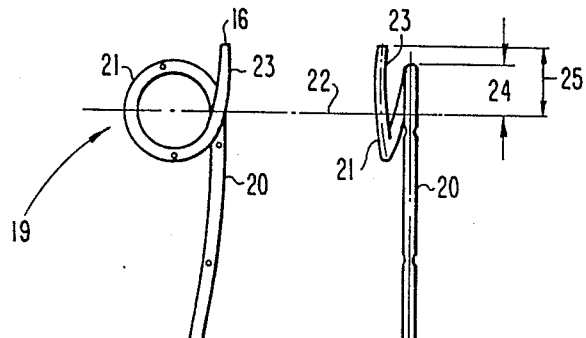
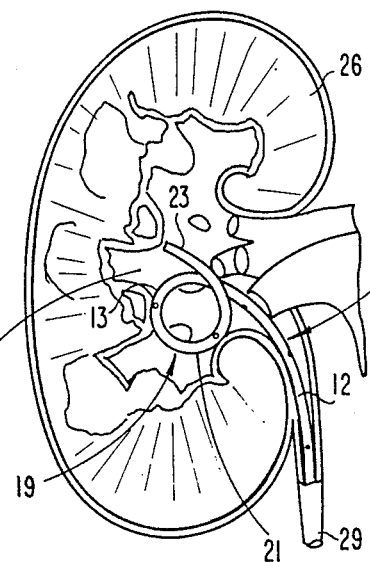
Fig.5
Fig.1  Fig.2
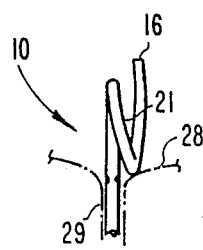
Fig.6
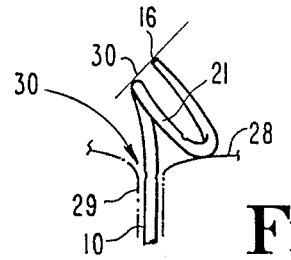
Fig.7
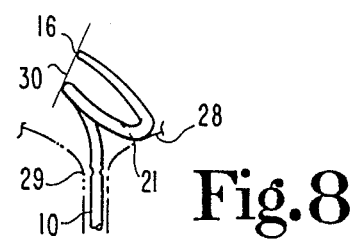
Fig.8
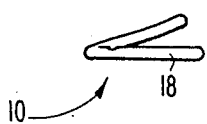
Fig.4
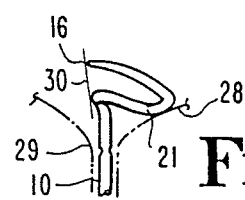
Fig.9

URETERAL STENT

BACKGROUND OF THE INVENTION

1. Field of the Invention

The present invention relates to the field of ureteral stents, and particularly to a stent having a novel distal curl which facilitates placement and removal of the stent within the kidney.

2. Description of the Prior Art

Indwelling ureteral catheter stents or drainage tubes have been used to bypass ureteral obstructions or ureteral-vaginal fistulas and maintain urinary drainage. In the past, stents made of straight lengths of open end tubing have been used for this purpose and have provided drainage for sustained periods of time. However, the use of such open end tubing has not been completely satisfactory. For example, in some instances the tubing has migrated and in others it has been expelled.

Various attempts have been made to produce stents which do not have the problems which accompany the use of such tubing. For example, stents have been designed which include an end flange to prevent migration of the stent. Another approach has been to provide the body of the stent with sharply pointed barbs which are designed to prevent migration and expulsion. However, such barbs increase the diameter of the stent, making it more difficult to insert and in some instances can cause the stent to migrate outside of the bladder. More recent stents have included a curve at one or both ends to prevent displacement.

Other important considerations with a ureteral stent are the ability to both accurately and conveniently place the stent, and readily remove the stent. These efforts will be significantly affected by the shape of the distal end of the stent. For example, hook-shaped or J-shaped kidney curls can present a problem when it is desired to remove the stent. The proximally-extending end of the curl can engage the interior of the kidney, such as in the area of the renal pelvis. Other prior art stents have been provided that include a full-circle or multiple curls. For these designs, it remains a factor that the shape of the distal curl may not be such as to prevent the tip from catching at the ureteropelvic junction. This can cause the stent to fold and kink in the ureter. Also, improper stent design can result in the stent being pulled into the ureter with the curl folded on itself.

In U.S. Pat. Nos. 4,212,304, issued July 15, 1979, and 4,307,723, issued on Dec. 29, 1981, there are disclosed ureteral stents which have hooks at each end which are provided for preventing migration and expulsion. Stents of this general type have been generally accepted because they can be easily introduced endoscopically and during open surgery. A ureteral stent having proximal and distal ends in the form of hooks and having open lumen at both ends is described in U.S. Pat. No. 4,610,657 issued to Densow on Sept. 9, 1986.

In U.S. Pat. No. 4,790,810 issued to Pugh, Jr., et al. on Dec. 13, 1988, there is disclosed a ureteral connector stent of adjustable length. The connector stent comprises an elongated, straight tubular member and a connector provided for coupling the tubular member with a curled end. As shown in the Pugh Patent, the curled end is generally in a helical shape, with the distal tip curling less than a full 360°.

Various stents having end curls have been made available in commercial embodiments. A ureteral stent sold under the mark UROPASS is available from Surgitek of Racine, Wis., and includes a kidney curl with the distal tip being positioned at a right angle to the stent body and extending a short distance across the body. Other prior art stents have included a pigtail curl at the distal end which has the distal tip formed in a 360° curve. Still others have provided distal curls in excess of 360°, and ranging from approximately one and one quarter turns to as many as two or three full turns. Helical ureteral stents of these general types are disclosed in U.S. Pat. Nos. 4,531,933, issued to Norton, et al. on July 30, 1985, and 4,813,925, issued to Anderson, Jr., et al. on Mar. 21, 1989.

The present invention is based on the discovery that a particular kidney curl design satisfies the various needs for a ureteral stent in a manner not previously available. The novel curl design facilitates placement and removal of the stent to an extent not afforded by the prior art.

SUMMARY OF THE INVENTION

Briefly describing one aspect of the present invention, there is provided a ureteral stent comprising an elongated tubular member having a substantially uniform outer diameter, proximal end retention means for retaining the proximal end in a bladder, and distal end retention means for retaining the distal end in a kidney, the distal end retention means including a first straight portion, a second portion extending from the first, and forming a 360° helical curl, and a third portion extending from the second and terminating in a distal tip, the third portion being straight and extending parallel to the first portion.

It is an object of the present invention to provide a ureteral stent which includes a distal curl shaped to be properly receivable in the kidney and to facilitate placement of the distal tip in the renal pelvis or calyx of choice.

A further object of the present invention is to provide a stent having a helical renal curl and extended tip to ensure easy and non-traumatic removal through the ureter, and particularly to prevent kinking of the stent upon removal.

Further objects and advantages of the present invention will be apparent from the description of the preferred embodiment which follows.

BRIEF DESCRIPTION OF THE DRAWINGS

FIG. 1 is a front elevational view of a ureteral stent constructed in accordance with the present invention.

FIG. 2 is a right side view of the stent of FIG. 1.

FIG. 3 is a distal end view of the stent of FIG. 1.

FIG. 4 is a proximal end view of the stent of FIG. 1.

FIG. 5 is a cross-sectional view of a kidney showing a proper placement of the ureteral stent of the present invention.

FIGS. 6–9 are partial left side views of the distal end portion of the ureteral stent of FIG. 1, and showing the manner in which the distal curl is withdrawn from the kidney.

DESCRIPTION OF THE PREFERRED EMBODIMENT

Figure 10:
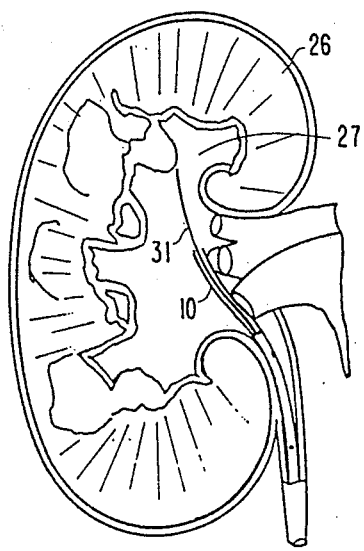
FIGS. 10–12 are cross-sectional views of a kidney and ureter showing in progression the manner of placement of the ureteral stent of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides a ureteral stent comprising an elongated tubular member having a generally straight body portion and opposed end portions with means for retaining the respective ends in the bladder and kidney. The bladder end of the ureteral stent may have any of a variety of configurations providing the desired retaining effect. It is a particular aspect of the present invention that the distal end portion has a particular renal curve which advantageously serves several functions. The curved portion provides means for retaining the distal end in the kidney. The distal tip of the stent is positioned to face away from the ureteral opening and extending tangentially from the helical curl to facilitate placement and removal of the stent. The cooperative effect of the helical nature of the curl and the positioning of the distal tip allows the curl to uncoil in the renal pelvis without kinking or being pulled down intact into the ureter.

Referring in particular to the drawings, there is shown a ureteral stent 10 constructed in accordance with the present invention. The stent comprises an elongated tubular member 11 of substantially uniform outside diameter throughout its length. The tubular member may be formed from a variety of known materials which are biocompatible and have desired physical properties to be fabricated in the form hereafter described. An example of a suitable material is a teflon material marketed by DuPont under the trademark Silitek®, which combines the longitudinal rigidity necessary for stenting difficult obstructions with the softness necessary for patient comfort.

The stent 10 includes a center body portion 12 which is positionable within the ureter. The body portion is preferably a substantially straight portion, but having sufficient flexibility to be passed into the ureter. The stent includes a central lumen communicating with several holes 14 along the length of the tubular member 11. The ureteral stent 10 thereby provides fluid communication along its length from the distal end to the proximal end. The stent is formed from a radiopaque material to permit visualization by X-ray, and may include a center line 13 placed along the length of the stent which may be viewed cystoscopically. The central lumen may extend fully to the proximal tip 15 and distal tip 16, although that is not essential. When the stent is placed within the ureter with the proximal end in the usual fashion, fluid communication is provided by means of the central lumen and the holes 14 and, when provided, the end openings at the proximal and distal tips.

The stent includes a proximal end 17 which is provided with retention means for retaining the proximal end in the bladder. This retention means may assume a variety of forms such as those commonly used in the prior art. For example, the proximal end may include a J-shaped curve 18. Holes 14 are also provided in the proximal end portion of the stent.

The ureteral stent also includes a distal end 19 which includes retention means for retaining the distal end in the kidney. This distal end retention means comprises the distal end being set in the shape of a helical curl with the distal end having three portions. The first, body portion 20 is a continuation of the body 12 of the stent and is substantially straight in the relaxed condition. The second, helical curl portion 21 extends from the first portion 20 and is in the shape of a 360° helical curl. The helical nature of the curl is shown particularly in FIGS. 2–4, and its function is explained hereafter, particularly with respect to FIGS. 6–9. The second portion 21 begins and ends at position 22, in line with the center of the helical curl. The third, extended tip portion 23 of distal end 19 extends from the second portion 21 at location 22 and terminates in the distal tip 16. This third portion 23 is substantially straight and parallel to the first portion 20.

As shown particularly in FIGS. 1 and 2, the distal tip 16 extends beyond the tangent point 22 of the helical curl and faces away from the body of the stent. The curl 21 has an outside radius as shown at 24. The extended tip portion 23 extends from the tangent position 22 and has a length 25 between 1.2 and 2.0 times the outside radius 24. A preferred length of the distal tip portion 23 is 1.6 times the outside radius 24 of the helical curl 21.

A proper placement of the ureteral stent 10 in a kidney 26 is shown in FIG. 5. The distal end 19 is received within the renal cavity 27 with the extended tip portion 23 facing away from the ureteropelvic junction. The holes 13 provide for fluid communication through the lumen of the stent down through the ureter to the bladder. The helical curl portion 21 retains the distal end of the stent in the kidney. Also, the configuration of the distal end of the stent, particularly the extended tip portion 23, permits easy placement of the distal tip in the renal pelvis or calyx of choice.

The distal end 19 provides a particular configuration for the retention means that is advantageous for placement and removal of the ureteral stent. Referring in particular to FIGS. 6–9, it is shown that the combination of the helical curl and extended distal tip insures easy stent removal. While in the renal cavity, the helical curl 21 fits comfortably within the renal pelvis 28.

Withdrawal of the stent 10 is accomplished simply by pulling the stent downwardly through the ureter 29. In this process, the offset of the curl, due to its helical form, will cause the curl to displace to the side, as shown in FIG. 7 as the stent is pulled down into the ureter. Because the distal tip 16 extends beyond the tangent location 22, it is positioned well clear of the ureteropelvic junction 30 as the curl begins to displace. This prevents the distal tip from catching in the ureteropelvic junction. This in turn prevents the curl from being kinked or folded upon itself and being pulled down into the ureter without first uncoiling.

For prior art devices which have the distal tip terminating at the location 22, it has been possible for the distal tip to be pulled down into the ureteropelvic junction and either to get caught or be pulled in a folded condition into the ureter. As shown particularly in FIGS. 8 and 9, the sideward displacement of the helical coil normally urges the distal tip in a downward direction towards the ureteropelvic junction, and absence of the extended tip of the present invention can result in the distal tip being urged into engagement with the ureteropelvic junction. In contrast, the presence of the extended tip portion 23 of the present invention avoids this problem and prevents the tip from being pulled into engagement with the ureteropelvic junction.

In addition, it will be noted from FIGS. 7–9 that the relative sizes of the extended tip 23 and helical curl 21 also cooperate to prevent engagement of the distal tip 16 within the renal cavity. The relative length of the distal tip portion 23 is such that the tip 16 does not extend substantially beyond the edge of the curl, as shown for example by the lines 30 in FIGS. 7–9. In other words, the size and position of the curl 21, relative to the location of the tip 16, provides a barrier to prevent the tip 16 from hanging up on a portion of the renal cavity.

Figure 11:
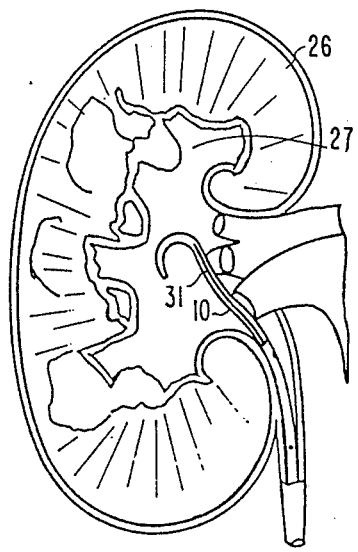
Figure 12:
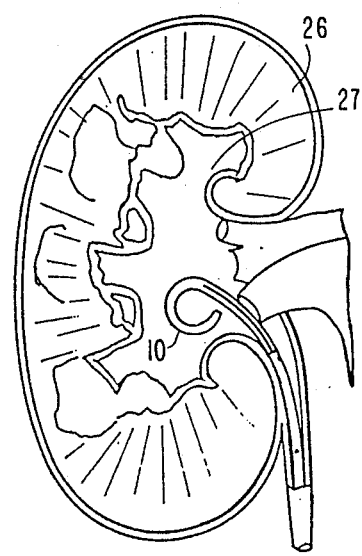

The placement of the ureteral stent 10 of the present invention may be accomplished in accordance with known prior art techniques. As shown for example in FIGS. 10–12, along with FIG. 5, the stent may be placed in position by advancement over a wire guide 31. The stent is formed from a material which is sufficiently flexible as to permit the helical curl 21 and the J-shaped curl 18 to retain their shape in a relaxed condition, but also to flex sufficiently as to be received over a wire guide. The wire guide 31 is positioned appropriately within the renal cavity and the stent 10 is gradually advanced over the wire guide. The wire guide is then removed, and the renal curl 21 will reform, as shown in FIGS. 10–12 and 5.

Proper placement of the distal tip 16 and the helical curl 21 is readily accomplished by proper positioning of the wire guide as the stent is advanced thereover. The center line 13 facilitates this placement by enabling the physician to cystoscopically determine the orientation of the uncoiled stent prior to withdrawal of the wire guide. For example, it is apparent from FIG. 2 that the position for the guideline 13 indicates that the distal end 19 will curl in the direction away from the centerline as the wire guide is removed. The wire guide is removed after the stent is placed over it, allowing the curl to reform and enabling the distal tip 16 and helical curl 21 to be positioned as desired.

The present invention provides a ureteral stent which is useful in a variety of applications to provide drainage from the kidney to the bladder. The stent can be used to bypass an obstruction or severe stricturing of the ureter. The present design allows for ready placement and removal of the stent, and will prevent migration of the stent while in place. The distal helical curl 21 and the J-shaped or other retention form on the proximal end preferably extend in opposite lateral directions from the body, permitting the distal helical curl to seat in the lower calyx or renal pelvis while the proximal curl lays below the ureteral vessical junction. The curls form distally in a lateral direction into the kidney and proximally in a medial direction into the bladder, which minimizes the risk of migration.

Although sizes are not critical, suitable dimensions for the ureteral stent of the present invention would include internal diameters of 4.0 to 5.5 French, outer diameters of 6.0 to 8.5 French, and lengths ranging from 22 cm. to 26 cm. The stent is preferably provided with an internal diameter tapered tip designed to allow passage of the stent in a retrograde manner. The distal tip 16 may be provided with a rounded tapered tip to facilitate passage. Drainage holes are preferably located about every 2 cm.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A ureteral stent for providing drainage communication between the kidney and the bladder, which comprises:

an elongated tubular member of substantially uniform outside diameter throughout its length, said member having proximal and distal ends connected by a body portion, the proximal end including retention means for retaining the proximal end in the bladder, the distal end including retention means for retaining the distal end in the kidney, the distal end retention means comprising the distal end being set in the shape of a helical curl and having three portions, the first portion extending from the body portion and being substantially straight, the second portion extending from the first portion and being in the shape of a 360° helical curl having an outside radius, and the third portion extending from the second portion and terminating in a distal tip, the third portion being substantially straight and parallel to the first portion, the third portion being in length between 1.2 and 2.0 times the outside radius of the helical curl of the second portion, said member including a central lumen and a plurality of holes communicating with the lumen to provide fluid communication between the proximal and distal ends.

2. The ureteral stent of claim 1 in which the third portion of the distal end is in length 1.6 times the outside radius of the helical curl.

3. The ureteral stent of claim 1 in which said tubular member has an outside diameter of between about 6.0 and about 8.5 French.

4. The ureteral stent of claim 1 and which is radiopaque.

5. The ureteral stent of claim 4 in which the third portion of the distal end is in length 1.6 times the outside radius of the helical curl.

6. The ureteral stent of claim 1 in which the proximal end retention means comprises the proximal end being set in a J-shaped curl.

7. The ureteral stent of claim 6 in which the third portion of the distal end is in length 1.6 times the outside radius of the helical curl.

8. The ureteral stent of claim 6 in which the helical curl and the J-shaped curl extend in opposite lateral directions from the body portion.

* * * * *